United States Patent
Kwok et al.

(10) Patent No.: US 10,858,441 B2
(45) Date of Patent: Dec. 8, 2020

(54) METHOD OF TREATMENT FOR PANCREATIC CANCER BY ADMINISTERING A HUMAN-MOUSE CROSS-REACTIVE ADAM 17 ANTIBODY

(71) Applicant: UNIVERSITY OF MACAU, Macau (CN)

(72) Inventors: Hang Fai Kwok, Macau (CN); Ruiyu Xie, Macau (CN)

(73) Assignee: University of Macau, Macau (CN)

( * ) Notice: Subject to any disclaimer, the term of this patent is extended or adjusted under 35 U.S.C. 154(b) by 0 days.

(21) Appl. No.: 16/033,654

(22) Filed: Jul. 12, 2018

(65) Prior Publication Data

US 2019/0375848 A1    Dec. 12, 2019

Related U.S. Application Data

(60) Provisional application No. 62/531,432, filed on Jul. 12, 2017.

(51) Int. Cl.

| C07K 16/28 | (2006.01) |
|---|---|
| A61K 31/7068 | (2006.01) |
| A61K 31/519 | (2006.01) |
| A61K 31/517 | (2006.01) |
| A61K 39/395 | (2006.01) |
| A61K 31/437 | (2006.01) |
| A61P 35/00 | (2006.01) |
| A61K 31/513 | (2006.01) |
| A61K 39/00 | (2006.01) |
| A61K 31/282 | (2006.01) |

(52) U.S. Cl.
CPC ........ *C07K 16/2896* (2013.01); *A61K 31/282* (2013.01); *A61K 31/437* (2013.01); *A61K 31/513* (2013.01); *A61K 31/517* (2013.01); *A61K 31/519* (2013.01); *A61K 31/7068* (2013.01); *A61K 39/3955* (2013.01); *A61P 35/00* (2018.01); *A61K 2039/505* (2013.01); *C07K 2317/33* (2013.01); *C07K 2317/76* (2013.01)

(58) Field of Classification Search
None
See application file for complete search history.

(56) References Cited

FOREIGN PATENT DOCUMENTS

WO    WO2015097287    *    7/2015    ........... A61K 39/395

OTHER PUBLICATIONS

Kwok et al. Development of a 'mouse and human cross-reactive' affinity-matured exosite inhibitory human antibody specific to TACE (ADAM17) for cancer immunotherapy. Protein Engin. Design & Selection, 27, 179-190, 2014. (Year: 2014).*
Faris et al., FOLFIRINOX in Locally Advanced Pancreatic Cancer: The Massachusetts General Hospital Cancer Center Experience. The Oncologist, 18, 543-548, 2013. (Year: 2013).*
Mountzios et al. A Benefit-Risk Assessment of Erlotinib in Non-Small-Cell Lung Cancer and Pancreatic Cancer. Drug Safety, 34, 175-186, 2011. (Year: 2011).*

* cited by examiner

*Primary Examiner* — Elly-Gerald Stoica
(74) *Attorney, Agent, or Firm* — Ladas & Parry LLP

(57) ABSTRACT

Pancreatic ductal adenocarcinoma (PDAC) is one of the most lethal types of tumor amongst all human cancers due to late diagnosis and resistant to treatment with chemotherapy and radiation. Preclinical and clinical studies have revealed that ErbB family for example epidermal growth factor receptor (EGFR) is a validated molecular target for pancreatic cancer prevention and therapy. The ErbB signaling cascade is regulated by a member of the ADAM (a disintegrin and metalloprotease) family, namely ADAM17, by enzymatic cleavage of precursor ligands into soluble cytokines and growth factors. Mouse genetic studies have demonstrated that ADAM17 is required for PDAC development. In this study, we evaluated the anti-tumor effects of A9(B8) IgG—the first specific 'human and mouse cross-reactive' ADAM17 inhibitory antibody on pancreatic malignant transformation. We found that inhibition of ADAM17 with A9(B8) IgG efficiently suppressed the shedding of ADAM17 substrates both in vivo and in vitro. Furthermore, we demonstrated that administration of A9(B8) IgG significantly suppressed motility in human pancreatic cancer cells and also significantly delayed tumorigenesis in the Pdx1Cre; KrasG12D;Trp53fl/+ PDAC mouse model. Inhibition of ADAM17 with A9(B8) IgG particularly affected the progression of pre-invasive pancreatic lesions to advanced PDAC in mice. Taken together, the preclinical data presented here will provide a starting point for clinical applications of ADAM17 targeted therapy.

4 Claims, 6 Drawing Sheets
(2 of 6 Drawing Sheet(s) Filed in Color)
Specification includes a Sequence Listing.

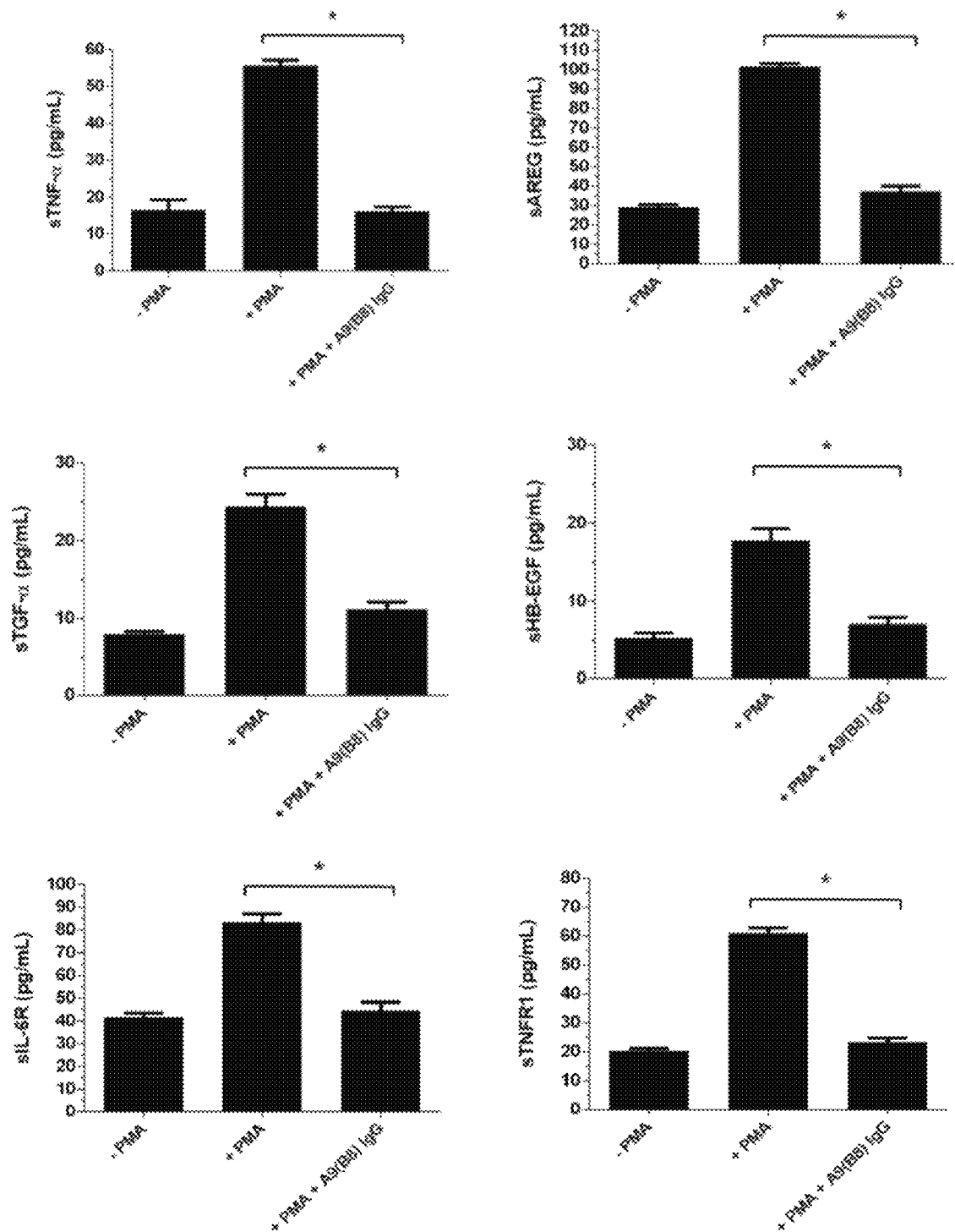
Figure 1. A9(B8) IgG inhibited PMA-induced shedding of ADAM17 substrates into PANC-1 cell culture medium.

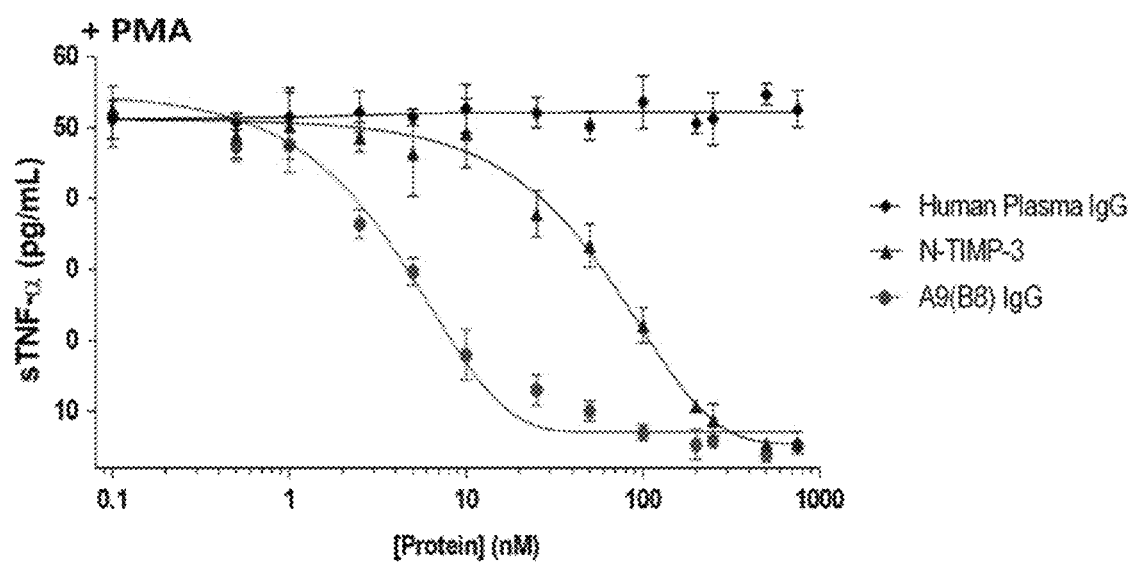
Figure 2. A9(B8) IgG inhibited TNF-α shedding in a dose-dependent manner.

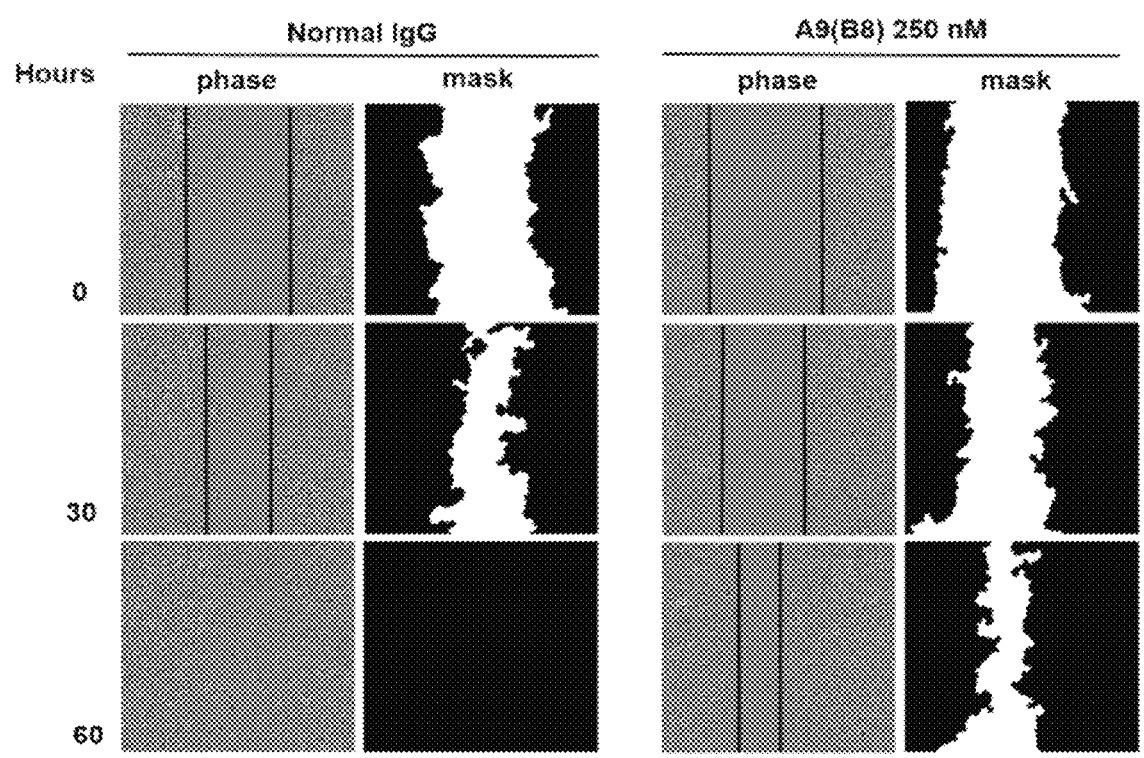
Figure 3. A9(B8) IgG inhibited the motility of PANC-1 cells.

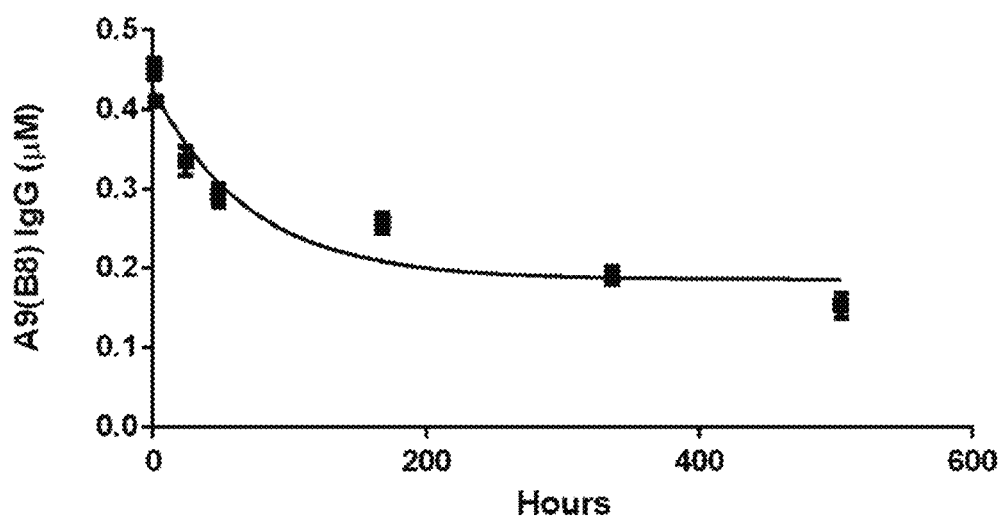
Figure 4. A Pharmacokinetic analysis of A9(B8) antibody in mice.

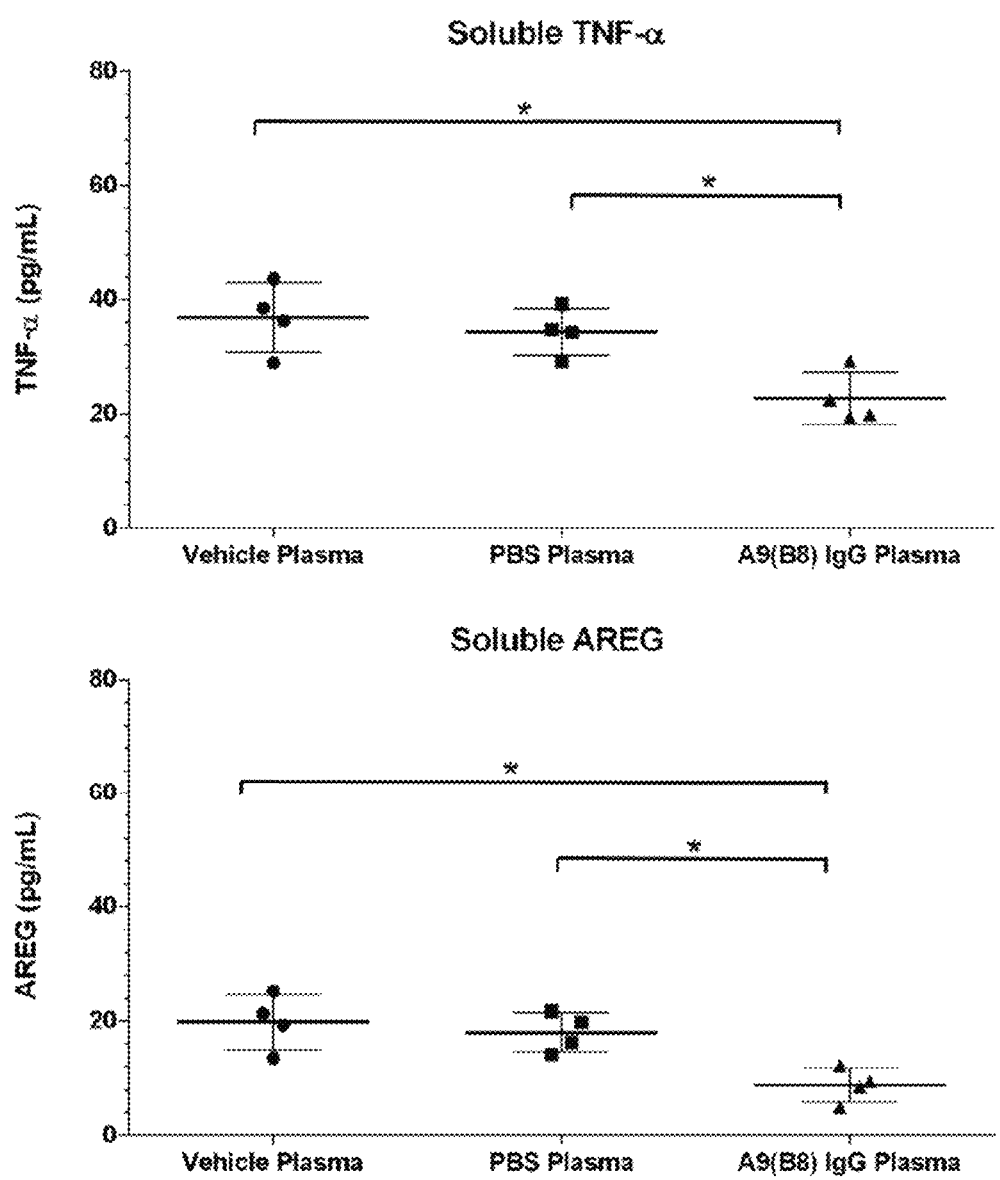
Figure 5. TNF-α and AREG were reduced in $Pdx1Cre;Kras^{G12D};Trp53^{flox/+}$ mice treated with A9(B8) IgG.

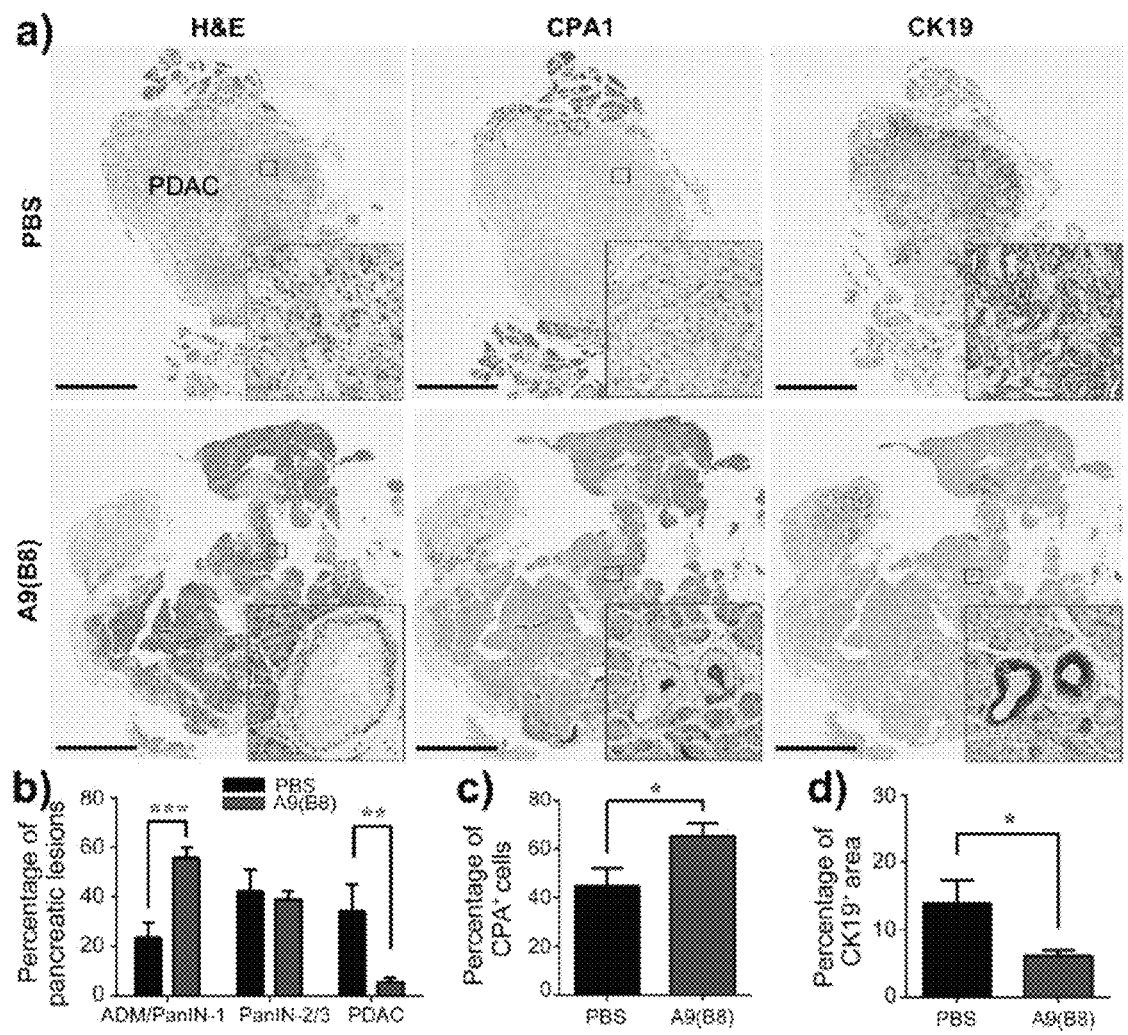
Figure 6. Inhibition of ADAM17 by A9(B8) IgG suppressed PDAC development.

SEQUENCE LISTING

```
<160> NUMBER OF SEQ ID NOS: 2

<210> SEQ ID NO 1
<211> LENGTH: 454
<212> TYPE: PRT
<213> ORGANISM: Artificial Sequence
<220> FEATURE:
<223> OTHER INFORMATION: Synthetic: A9(B8) Heavy chain

<400> SEQUENCE: 1

Gln Val Thr Leu Lys Glu Ser Gly Gly Gly Leu Phe Gln Pro Gly Gly
1               5                   10                  15

Ser Leu Arg Leu Ser Cys Ala Ala Ser Gly Phe Thr Phe Ser Asn Tyr
            20                  25                  30

Trp Met Tyr Trp Val Arg Gln Ala Pro Gly Lys Gly Pro Glu Trp Val
        35                  40                  45

Ala Thr Ile Lys Gln Asp Gly Ser Asp Lys Tyr Tyr Val Asp Ser Val
    50                  55                  60

Lys Gly Arg Phe Thr Ile Ser Arg Asp Asn Thr Lys Asn Ser Leu Tyr
65                  70                  75                  80

Leu Gln Met Asn Ser Leu Arg Ala Asp Thr Ala Met Tyr Tyr Cys
                85                  90                  95

Ala Arg Ser Arg Glu Arg Tyr Ser Val Asp Ser Tyr Leu Pro Leu His
            100                 105                 110

Tyr Tyr Met Asp Val Trp Gly Arg Gly Thr Met Val Thr Val Ser Ser
        115                 120                 125

Ala Ser Thr Lys Gly Pro Ser Val Phe Pro Leu Ala Pro Cys Ser Arg
    130                 135                 140

Ser Thr Ser Glu Ser Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
                165                 170                 175

Gly Val His Thr Phe Pro Ala Val Leu Gln Ser Ser Gly Leu Tyr Ser
```

```
                180             185             190
Leu Ser Ser Val Val Thr Val Pro Ser Ser Asn Phe Gly Thr Gln Thr
            195                 200                 205
Tyr Thr Cys Asn Val Asp His Lys Pro Ser Asn Thr Lys Val Asp Lys
    210                 215                 220
Thr Val Glu Arg Lys Cys Cys Val Glu Cys Pro Pro Cys Pro Ala Pro
225                 230                 235                 240
Pro Val Ala Gly Pro Ser Val Phe Leu Phe Pro Pro Lys Pro Lys Asp
                245                 250                 255
Thr Leu Met Ile Ser Arg Thr Pro Glu Val Thr Cys Val Val Val Asp
            260                 265                 270
Val Ser His Glu Asp Pro Glu Val Gln Phe Asn Trp Tyr Val Asp Gly
        275                 280                 285
Val Glu Val His Asn Ala Lys Thr Lys Pro Arg Glu Glu Gln Phe Asn
    290                 295                 300
Ser Thr Phe Arg Val Val Ser Val Leu Thr Val Val His Gln Asp Trp
305                 310                 315                 320
Leu Asn Gly Lys Glu Tyr Lys Cys Lys Val Ser Asn Lys Gly Leu Pro
                325                 330                 335
Ala Pro Ile Glu Lys Thr Ile Ser Lys Thr Lys Gly Gln Pro Arg Glu
            340                 345                 350
Pro Gln Val Tyr Thr Leu Pro Pro Ser Arg Glu Glu Met Thr Lys Asn
        355                 360                 365
Gln Val Ser Leu Thr Cys Leu Val Lys Gly Phe Tyr Pro Ser Asp Ile
    370                 375                 380
Ala Val Glu Trp Glu Ser Asn Gly Gln Pro Glu Asn Asn Tyr Lys Thr
385                 390                 395                 400
Thr Pro Pro Met Leu Asp Ser Asp Gly Ser Phe Phe Leu Tyr Ser Lys
                405                 410                 415
Leu Thr Val Asp Lys Ser Arg Trp Gln Gln Gly Asn Val Phe Ser Cys
            420                 425                 430
Ser Val Met His Glu Ala Leu His Asn His Tyr Thr Gln Lys Ser Leu
        435                 440                 445
Ser Leu Ser Pro Gly Lys
    450

<210> SEQ ID NO 2
<211> LENGTH: 216
<212> TYPE: PRT
<213> ORGANISM: Artificial Sequence
<220> FEATURE:
<223> OTHER INFORMATION: Synthetic: A9(B8) Light chain

<400> SEQUENCE: 2

Gln Ser Val Leu Thr Gln Pro Pro Ser Ala Ser Gly Thr Pro Gly Gln
1               5                   10                  15
Arg Val Thr Ile Ser Cys Ser Gly Ser Ser Ser Asn Ile Gly Ser Asn
            20                  25                  30
Thr Val Asn Trp Tyr Gln Arg Leu Pro Gly Ala Ala Pro Gln Leu Leu
        35                  40                  45
Ile Tyr Asn Asn Asp Gln Arg Pro Ser Gly Ile Pro Asp Arg Phe Ser
    50                  55                  60
Gly Ser Lys Ser Gly Thr Ser Gly Ser Leu Val Ile Ser Gly Leu Gln
65                  70                  75                  80
Ser Glu Asp Glu Ala Asp Tyr Tyr Cys Ala Ser Trp Asp Asp Ser Leu
```

```
                        85                      90                      95
Asn Gly Arg Val Phe Gly Gly Thr Lys Leu Thr Val Leu Gly Gln
                100                     105                 110

Pro Lys Ala Ala Pro Ser Val Thr Leu Phe Pro Pro Ser Ser Glu Glu
        115                     120                 125

Leu Gln Ala Asn Lys Ala Thr Leu Val Cys Leu Ile Ser Asp Phe Tyr
    130                     135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
210                 215
```

METHOD OF TREATMENT FOR PANCREATIC CANCER BY ADMINISTERING A HUMAN-MOUSE CROSS-REACTIVE ADAM 17 ANTIBODY

CROSS REFERENCE TO RELATED APPLICATION

The present application claims priority from provisional application 62/531,432 filed on Jul. 12, 2017, the contents of which are incorporated herein by reference.

REFERENCE TO SEQUENCE LISTING SUBMITTED VIA EFS-WEB

This application includes an electronically submitted sequence listing in .txt format. The .txt file contains a sequence listing entitled "U_020178-7_ST25.txt" created on Aug. 27, 2019 and is 6,345 bytes in size. The sequence listing contained in this .txt file is part of the specification and is hereby incorporated by reference herein in its entirety.

SEQUENCE LISTINGS

This application includes sequence listing SEQ ID NO:1 and SEQ ID NO:2.

FIELD OF THE INVENTION

The present invention relates to treatment for pancreatic cancer.

BACKGROUND

Pancreas cancer is virtually fatal within a very short time after diagnosis due to the late stage detection and resistance to most chemo- and radiation therapies (Janes et al., 1996). The most common type of pancreatic cancer, pancreatic ductal adenocarcinoma (PDAC), accounts for over 90% of all pancreatic malignancies. PDAC represents the fourth cause of death in cancer, with an overall 5-year survival rate of <5% (Warshaw and Fernandez-del Castillo, 1992). Surgical resection with radiation therapy or chemotherapy remains the only potential curative treatment today (Hidalgo, 2010). However, only 5% to 25% of patients with resectable tumors and the median survival of these patients is less than 2 years, predominantly due to the local and systemic recurrence after surgery. Although the addition of erlotinib or other EGFR inhibitors with gemcitabine has proven to provide modest benefits to PDAC treatment, many patients rapidly acquired resistance to this combination therapy (Moore et al., 2007; Wang et al., 2015). Therefore, better management strategies and more effective treatments for PDAC are urgently needed.

PDAC is preceded by the formation of non-invasive premalignant lesions; in particular pancreatic intraepithelial neoplasias (PanINs), the most common pancreatic precursor lesions. Based on histological analysis, PanINs can be classified into two pathological stages, low-grade PanINs (PanIN-1 and PanIN-2), and high-grade PanINs (PanIN-3) (Basturk et al., 2015; Cornish and Hruban, 2011; Koorstra et al., 2008). Overwhelming experimental evidence suggests that PanINs predominantly arise from acinar cells through a process referred as acinar-to-ductal metaplasia (ADM) which is characterized by the loss of acinar markers, carboxypeptidase A1 (CPA1) and amylase, and gain in expression of ductal markers SOX9 and cytokeratin-19 (CK19) (Kopp et al., 2012; Zhu et al., 2007). The transformation of pancreatic acini to dysplastic epithelium accompanies with a well-characterized sequence of genetic changes, including the activation of proto-oncogene KRAS and subsequent loss of various tumor suppressor genes P16INK4A, TRP53, SMAD4 or BRCA2 (Hruban et al., 2000). Genetically engineered mouse models expressing oncogenic Kras together with conditional deletion of Trp53 have been shown to recapitulate the step-wise development of human pancreatic tumors (Bardeesy et al., 2015; Morton et al., 2008).

Upstream of KRAS, ErbB-mediated signaling cascades for example epidermal growth factor receptor (EGFR) signaling cascades play an important role for pancreatic tumorigenesis. Without EGFR activation, mutant KRAS could not efficiently drive tumorigenesis of pancreas in vivo (Ardito et al., 2012; Navas et al., 2012). These pre-clinical studies have suggested that EGFR is a validated molecular target in pancreatic tumorigenesis. Combination of an EGFR tyrosine kinase inhibitor or erlotinib, with gemcitabine demonstrated a significant survival benefit in several clinical studies (Moore et al., 2007; Wang et al., 2015). However, constant EGFR inhibition leads to tumor resistance after treatment. One possible explanation for the development of resistance is the activation of alternative EGF-family receptors via the release of their ligands.

Members of the ADAM (a disintegrin and metalloprotease) family of membrane-anchored sheddases are key regulators of ErbB signaling by proteolytic cleavage of membrane-anchored precursors of ErbB ligands into soluble cytokines and growth factors (Sahin et al., 2004). ADAM17 is a critical sheddase for the ErbB family-ligands transforming growth factor TGF-α, heparin binding epidermal growth factor-like growth factor (HB-EGF), and amphiregulin (AREG). Overexpression of ADAM17 and ErbB family-ligands is often found in various form of human cancer (Blanchot-Jossic et al., 2005; Borrell-Pages et al., 2003; McGowan et al., 2013;

Normanno et al., 2006; Zheng et al., 2007). A recent study has shown that genetic deletion of ADAM17 protects mice from PDAC development (Ardito et al., 2012).

Similar to mice with specific ablation of EGFR in acinar cells, ADAM17 knockout mice were protected from KRAS-driven pancreatic tumorigenesis and showed reduced levels of BrdU incorporation and cyclin D1 expression compared to ADAM17 wild-type mice (Ardito et al., 2012).

Due to the critical role ADAM17 plays in cancer, ADAM17 has been presented as a promising target for anti-tumor treatment (Blanchot-Jossic et al., 2005; Borrell-Pages et al., 2003; McGowan et al., 2013; Zheng et al., 2007). Several pharmacological inhibitors against ADAM17 have been developed over the past decade (DasGupta et al., 2009; Fridman et al., 2007; Liu et al., 2006; Zhou et al., 2006). Although these chemical inhibitors have achieved some success in pre-clinical studies, the results obtained from clinical trials have been disappointing and many of those have been terminated due to toxicity (Coussens et al., 2002; Zhang et al., 2004).

One possible mechanism of the resistance to EGFR inhibition is due to the stimulation of other ErbB family members or Notch signaling pathway through the elevation of metalloproteinase-mediated proteolytic cleavage of transmembrane ligands (Ardito et al., 2008; Sawey et al., 2007). Previous studies have shown that inhibition of different metalloproteinases, such as ADAM8, ADAM10 or ADAM17, suppresses pancreatic cancer cell proliferation, migration or invasion, suggesting that ADAMs are potential therapeutic targets for pancreatic cancer (Ardito et al., 2012; Schlomann et al., 2015; Woods et al., 2015). Moreover, it has been recently reported that after the chemotherapy treatment of pancreatic cancer cell line and a number of other cancer cell lines, there are significantly more ErbB ligands released as a result of an upregulation of the sheddase ADAM17 expression (Kyula et al., 2010; Van Schaeybroeck et al., 2011). It is therefore necessary to look for agents to specifically target ADAM17 for combination therapies.

The development and use of antibodies for targeted cancer therapy has gained a lot of attention in the past few decades because of their safety, high specificity and effectiveness across different models (Fauvel and Yasri, 2014; Neves and Kwok, 2015). A9(B8) antibody is the first 'human and mouse cross-reactive' specific anti-ADAM17 inhibitory antibody (Kwok et al., 2014). Due to the unique binding features of A9(B8) antibody along with the favorable pharmacokinetic (PK) properties that we showed in this study, this antibody serves perfectly as a prototype drug to target ADAM17 in preclinical studies with both in vitro human cell-based assays and an in vivo mouse model of PDAC. In this study, A9(B8) IgG efficiently prevented the release of a number of cytokines and ErbB ligands, such as TNF-α and AREG both in vitro and in vivo. Previous reports have also suggested that TNF-α expression was shown to be elevated during PDAC initiation process, and AREG was upregulated in pancreatic cancer to enhance pancreatic tumour growth through an autoregulated feedback loop (Busser et al., 2011; Funatomi et al., 1997; Zhao et al., 2016).

The unexpected outcome of those clinical trials was, at least partly, due to the non-specificity of ADAM17 inhibitors that cross-react with the closely related matrix metalloproteinases at the zinc-containing active site (Georgiadis and Yiotakis, 2008; Moss et al., 2008). To overcome this issue, we recently developed an antibody that specifically recognizes ADAM17, A9(B8) IgG. This antibody significantly inhibited ADAM17 activity and bound to ADAM17 more effectively than its parent antibody D1(A12) (Kwok et al., 2014). Additionally, A9(B8) IgG is cross-reactive in mouse and human, which allows pre-clinical studies to be carried out in murine cancer models. Application of anti-ADAM17 antibodies has been shown to reduce tumor growth in ovarian cancer, triple negative breast cancer cells, as well as head and neck squamous carcinoma (Kwok et al., 2014; Richards et al., 2012; Tape et al., 2011). In this study, we sought to investigate the effects of this anti-ADAM17 antibody, A9(B8), on a model of pancreatic tumorigenesis.

WO 2012/104581 describes use of the antibody D1(A12) which only recognizes the human ADAM17 but not mouse ADAM 17 as having potential use in treatment of cancers including pancreatic cancer.

WO2016/102716 and WO 2015/097287 both discuss use of a different ADAM17 antibody sequence from that forming the subject of the present invention for treatment of cancer. For examples, in WO2016/102716, the inventors documented that intraperitoneal injection of an anti-ADAM17 monoclonal antibody, m1022C3, inhibited tumor volume in a heterotopic subcutaneous xenograft model, suggesting that m1022C3 can inhibit pancreatic cancer cell proliferation. However, it has been found that the subcutaneous microenvironment is not relevant to that of the organ site of primary tumor. It has been consistently observed that drug regimens that are curative in mouse subcutaneous xenograft models often do not have a significant effect on human disease. Therefore, subcutaneous xenograft models that do not represent appropriate sites for human tumors are not predictive when used to test responses to anti-cancer drugs. In contrast, we used a well-established mouse model of pancreatic ductal adenocarcinoma (PDAC) to evaluate the therapeutic effects of our 'human and mouse cross-reactive' specific anti-ADAM17 antibody, A9(B8). The Similar to the development of human PDAC, our Pdx1Cre;Kras$^{G12D}$; Trp53$^{flox/+}$ (KP$^f$C) mice developed full spectrum of pancreatic lesions from low-grade and high-grade pancreatic intraepithelial neoplasias (PanINs) to advanced PDAC. We found that intravenous injection of A9(B8) IgG dramatically suppressed the transition of metaplastic acini into advanced epithelial neoplasia, implicating that inhibition of ADAM17 via A9(B8) IgG affects the progression of pre-invasive lesions to advanced PDAC.

Ardito et al in Cancer Cell vol 22 pp 304-317 (2012) discuss a mechanism whereby inhibition of ADAM17 may affect initiation of pancreatic ductal carcinoma by eliminating KRAS-driven tumorogenesis.

In Protein Engineering Design & Selection Vol 27 pp 179-190 (2014) the present inventor describes an ADAM17 inhibitor in the form of an A9IgG antibody having both human and murine immunoreactivity.

SUMMARY OF THE INVENTION

FIG. 1. In vitro activity of A9(B8) antibody in PANC-1 cells. (a) A9(B8) IgG inhibited PMA-induced shedding of ADAM17 substrates into PANC-1 cell culture medium. Medium was collected after 1 h incubation with PMA (100 ng/ml). A9(B8) IgG (200 nM) or solvent control. The substrates were quantified by ELISA. (b) A9(B8) IgG inhibited constitutive shedding of TNF-α from PANC-1 cells into culture medium. Medium was collected 48 hours after incubating cells with or without human plasma IgG (200 nM) or A9(B8) IgG (200 nM). Each data point represents the mean value of biological triplicate within a single experiment. (c) Dose-dependent inhibition of TNF-α shedding by 1 hour pretreatment with A9(B8) IgG, N-TIMP-3 or control human plasma IgG prior to PMA stimulation. Error bars 25 represent means±SEM of three replicates. Significant difference is indicated with brackets (*p<0.05).

FIG. 2. Effect of A9(B8) antibody on the growth and motility of PANC-1 cells. (a) Scratch wound assay was performed in 96-well plate using the IncuCyte live imaging system. PANC-1 cells were wounded 1 h after incubation with normal human plasma IgG control (250 nM) or A9(B8) IgG (250 nM). Images were taken at 2 hourly intervals, with representative images at 0 h, 30 h and 60 h, intervals being shown. The mask images were automatically generated by the IncuCyte Zoom software at 0 h, 30 h and 60 h. (b) Quantitative analysis of gap size of the wounds was shown. The value of gap size obtained at 60 h were normalised by values obtained at 0 h for each treatment. Error bars represent means±SEM of five replicates. Significant difference 26 is indicated with brackets (*p<0.05). (c) Cell proliferation assay was performed in 96-well plate using the IncuCyte live imaging system. Cells were seeded in 96-well plate with complete medium. A9(B8) IgG (250 nM) or normal human plasma IgG control (250 nM) were added 8 h after seeding. The confluence values were obtained by calculating the percentage of cell surface area coverage of each well. Each curve represents the mean confluence value of three replicates.

FIG. 3. A Pharmacokinetic analysis of A9(B8) antibody in mice. Following a single i.v. administration of A9(B8) using a bi-exponential model (linear scale), it showed that initial half-life value of approximately 13 hours with a terminal half-life of approximately 10.5 days. Error bars represent SEM of four replicates.

FIG. 4. Pdx1Cre;KrasG12D;Trp3flox/+ mice develop full spectrum of pancreatic lesions. H&E staining of pancreatic sections of 1-, 2- and 3-month-old KPflC mice, showing that low-grade PanINs (arrow in a and higher magnification in b), high-grade PanINs (asterisk in c and higher magnification in d), and advanced PDAC (arrowhead in e and higher magnification in f).

FIG. 5. In vivo activity of A9(B8) antibody. Reduction of soluble TNF-α and AREG by A9(B8) IgG was recorded. Serum was obtained from untreated mice (vehicle plasma) or mice treated with PBS or A9(B8) IgG. The level of TNF-α and AREG was measured by ELISA. Error bars represent means±SEM of four replicates. Significant difference is indicated with brackets (*p<0.05).

FIG. 6. Inhibition of ADAM17 activity by A9(B8) suppresses PDAC development. (a) KRAS/P53-driven PDAC formation in A9(B8)-treated Pdx1Cre;KrasG12D;Trp53lox/+ mice compared to PBS-treated mice, shown by H&E (left panels, scale bars=2 mm), IHC staining for CPA1 (middle panels) and IHC staining for CK19 (right panels). Graphs represent quantitation of different categories of pancreatic precursor lesions (b). CPA1 positive cells (c) and CK19 positive area (d) in PBS-treated (n=13) or A9(B8)-treated (n=17) pancreata. Error bars represent means SEM. *p<0.001; p<0.01, *p<0.05, all other differences were not significant.

The present invention provides a treatment for pancreatic cancer, in particular pancreatic duct adrenal carcinoma such as pancreatic adenocarcinoma, which comprises administering to a patient in need thereof a therapeutically effective amount of a human-mouse cross reactive ADAM17 inhibitory antibody such as inhibitory antibody A9(B8) igG. Such antibody may be administered intravenously or subcutaneously. A suitable dosing amount for a subject can be, for example, 10-15 mg/kg, which can be administered by intravenous injection.

BRIEF DESCRIPTION OF THE FIGURES

The patent or application file contains at least one drawing executed in color. Copies of this patent or patent application publication with color drawings will be provided by the office upon request and payment of the necessary fee.

FIG. 1 shows in vitro activity of A9(B8) antibody in PANC-1 cells. (a) A9(B8) IgG inhibited PMA-induced shedding of ADAM17 substrates into PANC-1 cell culture medium.

FIG. 2. shows the effect of A9(B8) antibody on the growth and motility of PANC-1 cells.

FIG. 3. provides a pharmacokinetic analysis of A9(B8) antibody in mice.

FIG. 4. Pdx1Cre;KrasG12D;Trp53flox/+ mice develop full spectrum of pancreatic Lesions.

FIG. 5. shows in vivo activity of A9(B8) antibody. Reduction of soluble TNF-α and AREG by A9(B8) IgG.

FIG. 6. shows inhibition of ADAM17 activity by A9(B8) suppresses PDAC development.

The heavy chain of antibody A9B8 has sequence listing SEQ ID NO: 1

The light chain of antibody A9B8 has sequence listing SEQ ID NO: 2.

DETAILED DESCRIPTION OF THE INVENTION

The present invention provides a method for reducing or preventing pancreatic cancer in patients in need thereof which can be used independently of or in conjunction with treatments of hypertension by administration of an ADAM17 inhibitory antibody to a subject in need thereof. AngII infusion showed vascular ADAM17 induction, EGFR activation and ER stress, which were attenuated in mice treated with such antibodies.

Antibodies suitable for use in the present invention are human and mouse cross-reactive ADAM17 inhibitory antibodies and include A9B8. Antibody A9B8 is available from Prof Hang Fai Kwok's research group at the faculty of Health Sciences (FHS) University of Macau.

Such antibodies may be administered to subjects in need thereof by conventional methods for administration of antibodies such as subcutaneous or intravenous injection. Such antibodies are typically administered at dosages of from 1-50 mg/kg every three days, more commonly in the range 3-20 mg/kg every three days, for example in the range 10-15 mg/kg every three daysday. The antibody is typically administered in a saline or dextrose solution (for example a 5% dextrose solution) at a concentration of from 100-500 nmol/liter, preferably 150-350 nmol/liter, for example about 250 nmol/liter.

Treatment will typically last for from 7 to 60 days but will depend upon the condition of the patient. For example in some cases a treatment of from 14 to 45 days, such as from 21 to 35 days may be sufficient.

Apart from ADAM17, ADAMS, another member of the ADAM family, has also been reported to play a role in invasion and migration through the activation of the ERK1/2 pathway in PDAC (Schlomann et al., 2015). ADAMS is normally expressed at low level in the plasma membrane of ductal cells and, and, to a lesser extent, in islets and acinar cells. In PDAC tissue, ADAM8 is highly expressed in tubular complexes and cancer cells (Valkovskaya et al., 2007). In addition, when ADAM8 is activated, the substrate spectrum overlaps with that of ADAM17 and ADAM10 and cleaves proteins with immune function such as TNFR1 (Bartsch et al., 2010). The method of the present invention may therefore be beneficial when used in combination with therapies for pancreatic cancer with other chemotherapy agents and pave the way for the development of A9(B8) IgG-specific therapies for PDAC. For example the treatment may be used in combination with chemotherapy agents such as gemcitabine, FOLFORINOX or Fluorouracil (5FU) as discussed in Cancer Treat Rev. 2009 June, 45(4): 335-9, the contents of which are incorporated herein by reference. The method of the present invention may also be used in combination therapy with erlotnib (for example as sold under the trademark TARCEVA).

Experimental

Materials and Methods
1. Antibodies and Chemicals

Production of human anti-ADAM17 antibody A9(B8) has been described previously (Kwok et al., 2014). Briefly, A9(B8) IgG was expressed by transfection of HEK293 cells and the antibody was purified from conditioned medium by two Protein-A/G columns (GE Healthcare) and AKTA FPLC affinity chromatography (GE Healthcare), followed by dialysis in HEPES-buffered saline, pH 7.4 and filter-sterilized. Control human plasma IgG (R&D Systems 1-001-A) was used as a control in cell-based assays. N-TIMP-3 was prepared as described by Lee et al (Lee et al., 2001).
2. Cell Culture The PANC 1 cell line was obtained from the American Tissue Type Collection (ATCC) and maintained in Dulbecco's minimal essential medium (DMEM) (Gibco) supplemented with 100% fetal bovine serum (Gibco), 4 mM L-glutamine (Gibco), and 1% penicillin-streptomycin (Gibco) at 37° C. in a humidified atmosphere of 95% air and 5% CO2.

3. Cell-Surface Shedding Assays

To prepare for shedding assays carried out in PANC-1 cells, 1×105 cells/well were plated on 48-well plate with 320 d of medium for 18 h. Cells were then washed once with serum free media and incubated with 100 ng/ml phorbol 12-myristate 13-acetate (PMA) (Sigma) or PMA supplemented with 200 nM A9(B8) IgG or solvent control for 1 h. Soluble substrates were measured by sandwich Duoset kits (R&D systems) using the following kits: human TNF-α (TNFSF1A; cat. no. DY210), human soluble TNFR1-α (TNFRSF1A; cat. no. DY225), human TGF-α (cat. no. DY239), human AREG (cat. no. DY262), human IL-6R-α (cat. no. DY227) and human HB-EGF (cat. no. DY259) according to manufacturer's instructions.

Absorbance was measured at 450 nm using Tecan Infinite-200. This process was performed three times for each cell line. Graphs were generated using GraphPad Prism 6 software (version 6.01).

4. IncuCyte Cell Proliferation Analysis

PANC-1 cells were seeded at $5 \times 10^3$ cells per well in 96-well, clear bottomed, tissue culture plates (Thermo Fisher Scientific) in 100 µl complete growth medium.

After 8 h, cells were treated with 250 nM A9(B8) IgG or 250 nM normal human plasma IgG (R&D systems) for control. The plate was then inserted into the IncuCyte (Essen Bioscience) for real-time imaging, with three fields imaged per well under 10× magnification every 2 h for a total of 4 days. Data were analyzed using the IncuCyte Zoom software (version 2014a), which quantified cell surface area coverage as confluence values. All IncuCyte experiments were performed in triplicate.

5. Wound Healing Assay

Cells were assessed in wound healing scratch assays using the IncuCyte (Essen Bioscience). PANC-1 cells were seeded at 4×104 cells on the 96-well ImageLock plates (Essen BioScience; cat. no. 4379) and incubated in complete media (DMEM with 10% FBS, and 4 mM L-glutamine) for 8 h. Wounds were made using the 96-pin WoundMaker (Essen BioScience) 1 h after the plate was washed twice with PBS, and incubated with DMEM containing 15% Charcoal/dextran-treated FBS (HyClone), 1% penicillin-streptomycin (Gibco), 4 mM L-glutamine (Gibco), 250 nM normal human plasma IgG (R&D systems) or 250 nM A9(B8) IgG. Cell migration was monitored in real time by IncuCyte, and wound width was measured by the IncuCyte software Zoom (version 2014a).

6. Mouse Procedures

All mouse experiments described herein were approved by the University of Macau Animal Research Ethics Committees.

A pharmacokinetic (PK) study was performed to assess the stability and half-life of A9(B8) antibody in serum. Six week old male and female C57BL/6 mice (three male; three female) were housed in a temperature and humidity-controlled room for the duration of the study. Blood samples pre-bleed were taken from each animal before treatment with A9(B8) IgG. Each animal was treated with 10 mg/kg A9(B8) IgG by intravenous tail (i.v.) injection. Blood samples were collected in heparinized tubes at selected time points post-antibody-injection (1, 4, 24, and 48 hours and 7, 21, 28, 35, and 42 days). Samples were centrifuged following collection, and serum was stored at −80° C. until analysis by ELISA. Briefly, 40 nM of recombinant human ADAM17 (R&D Systems) was coated onto a 96-well plate and incubated with varying dilutions of serum or drug standards for 1 hour at room temperature. After rinsing with PBS-T, anti-Human IgG Antibody-Fc-HRP conjugate (Merk Millipore) was added to each well. Plates were incubated for 1 hour at room temperature, washed with PBS-T and then incubated with TMB for 5 minutes at room temperature. The reaction was stopped by the addition of 500 mmol/I HCL, and absorbance was read at 450 nm.

The Pdx1Cre;LSL-KravG12D;Trp53flox/+ mice have been described previously (Morton et al., 2008). Mice were intravenously administered with PBS or A9(B8) IgG diluted in PBS at 10 mg/kg of body weight per injection. Retro-orbital blood samples were collected from mice before A9(B8) IgG treatment at 5 week of age and after complete A9(B8) IgG treatment at 13 week of age. Serum was separated from the blood samples by spinning at 2500 rpm for 15 mins and stored at −80° C. for further ELISA analysis of TNF-α and AREG levels. PBS- or A9(B8) IgG-treated mice were sacrificed at different time points and pancreata were removed for immunohistochemical analyses.

7. Histology and Immunohistochemical Analysis

Pancreata specimens were fixed in 4% paraformaldehyde overnight and processed with ASP6025 Tissue processor (Leica). Paraffin-embedded sections were subject to hematoxylin and eosin (H&E) or immunohistochemical (IHC) staining.

Primary and secondary antibodies utilized for immunohistochemistry included the following: rabbit anti-CK19 (Abcam ab52625, 1:1000); goat-anti-CPA1 (R&D systems; cat no. AF2765; 1:1000); biotinylated anti-rabbit or anti-goat (Jackson ImmunoResearch Laboratories Inc., 1:500). High-resolution scans of entire slides were generated using a Leica SCN400F scanner and histological features were annotated using Aperio image scope software (version v12.1.0.5029). Whole slide images were analyzed to identify the presence of pancreatic precursor lesions as well as the quantification of CPA1 and CK19 positive staining. The percentage of CPA1 positive cells was quantified by the Aperio Cytoplasm Algorithm and the percentage of CK19 positive area was quantified by Aperio Positive Pixel Algorithm (https://htrc.uchicago.edu/Downloads/HTRC_cytoplasmicUG.pdf). At least five 20× images from each animal were analyzed.

8. Quantitative ELISA for In Vivo Study

Soluble TNF-α and AREG levels in mice were quantified by sandwich Duoset kits (R&D Systems): mouse TNF-α (TNFSF1A; cat. no. DY410) and mouse AREG (cat. no. DY989) according to manufacturer's instructions. Absorbance was measured at 450 nm using Tecan Infinite-200. Graphs were generated using GraphPad Prism 6 software (version 6.01).

9. Statistical Analysis

The differences observed between the normal IgG/PBS and A9(B8) IgG treated groups for ELISA data, wound healing assay and IHC staining were analysed using Student t-test (two-tailed) by GraphPad Prism 6 software (version 6.01). The results were expressed as the mean±SEM (standard error of mean) from at least three replicates and a value of $p<0.05$ was considered statistically significant.

Results

1 Effects of A9(B8) IgG on ADAM17 Catalytic Activity in PANC-1 Cells

The shedding activity of ADAM17 in pancreatic cancer cells was assessed by the release of cytokines, growth factors and receptors into the culture medium (FIG. 1a).

When stimulated with PMA, secretion of TNF-α, TGF-α, AREG, HB-EGF, TNFR1-α and IL-6R-α was increased at least 2-fold in human pancreatic cancer cells PANC-1. This PMA-stimulated shedding was effectively inhibited by the addition of 200 nM A9(B8) IgG (FIG. 1a). Constitutive shedding of TNF-α over a long period of time was also suppressed by A9(B8) (FIG. 1b). Furthermore, we found that A9 (B8) was more potent than a natural metalloproteinase inhibitor, N-TIMP-3, previously shown to specifically inhibit murine ADAM17 with an IC50 of 72 nM (FIG. 1c) (Kwok et al., 2014). These results imply that A9(B8) IgG is comparable to its parent antibody D1(A12) IgG with respect to the inhibitory efficiency of ADAM17-mediated shedding on cancer cells (Richards et al., 2012; Tape et al., 2011).

2. Effects of A9(B8) IgG on Cell Proliferation and Migration In Vitro

To investigate the effects of A9(B8) IgG on tumorigenic properties of pancreatic cancer cells, we first examined the proliferation and migration of PANC-1 cells in response to A9(B8) IgG treatment. Cell motility was assessed using a scratch-induced wound-healing assay in PANC-1 cells which harbor Kras, P16INK4A and Trp53 mutations. We found that treatment with 250 nM A9(B8) IgG led to a significant delay in wound closure compared to normal IgG control (FIGS. 2a and 2b). However, A9(B8) IgG did not affect the proliferation of PANC-1 cells (FIG. 2c), suggesting A9(B8) IgG-mediated impairment of wound-healing is not due to a decrease in cell proliferation. Similar results were also obtained from the other pancreatic ductal adenocarcinoma cell line, BxPC-3 (data not shown). These data demonstrated that inhibition of ADAM17 catalytic activity with A9(B8) IgG resulted in a substantial reduction in cell migration which was independent of cell growth.

Pharmacokinetics of a 9(B8) Antibody in Animal

In order to evaluate the potential serum half-life and blood clearance rates of A9(B8) IgG, a pharmacokinetic (PK) study was performed in C57BL/6 mice. The PK profile of each individual animal was analyzed as well as the analysis of pooled serum samples for each time point. Both methods of analyses gave similar PK profiles. Data analyzed by a bi-exponential model showed that the A9(B8) antibody has an initial half-life value of approximately 13 hours with a terminal half-life of approximately 10.5 days (FIG. 3). The results demonstrated that A9(B8) antibody can act as a prototype drug into experimental therapeutics with favorable pharmacokinetic properties.

3.4 Inhibition of ADAM17 by a 9(B8) Suppresses the Development of PDAC In Vivo.

To evaluate the effect of the ADAM17 inhibitory antibody A9(B8) on pancreatic tumor progression in vivo, we used genetic strategies to specifically induce expression of oncogenic Kras and simultaneously delete one allele of the Trp53 gene to generate a Cre-lox-based mouse pancreatic tumor model. Specifically, Pdx1Cre mice were crossed with mice harboring a loxP-flanked stop cassette followed by a G12D mutation in the Kras gene (LSL-KrasG12D) and a "floxed" allele of the Trp53 gene to generate Pdx1Cre;KrasG12D; Trp53flox/+(KPflC) mice. KPflC mice developed full spectrum of pancreatic lesions from low-grade and high-grade PanINs to advanced PDAC as previously demonstrated (FIG. 4) (Morton et al., 2008; Morton et al., 2010).

At one month of age, we began to observe the development of low-grade precursor lesions (FIG. 4).

To examine the effects of A9(B8) IgG on tumor progression to PDAC, from 5 weeks of age, KPflC mice were intravenously injected with PBS or A9(B8) IgG twice per week for 6 weeks and plasma levels of soluble TNF-α and AREG were measured.

Blood samples were collected before the first injection and 2 weeks after the last injection. Consistent with the observation that soluble TNF-α was reduced in vitro, mice treated with A9(B8) IgG displayed a significant decrease in TNF-α and AREG in blood plasma compared to PBS-treated mice (FIG. 5).

Histological changes of pancreata were analyzed by hematoxylin and eosin (H&E) from A9(B8) IgG- and PBS-treated mice two weeks after the last injection.

As shown in FIG. 6a, the vast majority of pancreata were histologically abnormal in PBS-treated mice, indicated by dispersed neoplastic lesions (FIG. 6a). Almost all KPflC mice (11 out of 13) treated with PBS developed invasive PDAC at 13 weeks of age. However, mice injected with A9(B8) IgG contained substantial areas of non-transformed tissue with occasional (4/17) development to advanced neoplastic lesions. Most of lesions in A9(B8) IgG-treated pancreata were ADM and pre-invasive PanINs. We classified all identified pancreatic lesions into three groups (earlier-stage lesions including ADM and PanIN-1, intermediate-stage lesions including PanIN-2 and PanIN-3 and advanced-stage lesions PDAC), and performed further statistical analysis. Interestingly, the occurrence of PDAC was dramatically decreased in A9(B8) IgG-treated mice compared to PBS-treated mice, while the number of ADM/PanIN-1 was significantly elevated in A9(B8) IgG-treated mice (FIG. 6b).

We also performed immunohistochemistry staining for the acinar cell marker carboxypeptidase A1 (CPA1) and ductal marker CK19. As expected, we observed significant loss of CPA1 expression and gain in expression of CK19 in all lesion area (FIG. 6a). We quantified the percentage of CPA1 positive cells and found that normal acinar cell area were significantly higher in A9(B8) IgG-treated mice in comparison with control mice (FIG. 6c). Consistent with containing more CPA1 positive normal acinar cells, A9(B8) IgG-treated pancreata displayed decreased CK19 positive ductal lesions compared to control (FIG. 6d). Together, these results indicated that inhibition of ADAM17 by A9(B8) IgG effectively prolongs the latency and decreases the frequency of PDAC formation in KPflC mice.

Discussion

It has been recently reported that after the chemotherapy treatment of pancreatic cancer cell line and a number of other cancer cell lines, there are significantly more ErbB ligands released as a result of an upregulation of the sheddase ADAM17 expression (Kyula et al., 2010; Van Schaeybroeck et al., 2011). It is therefore necessary to look for agents to specifically target ADAM17 for combination therapies.

The development and use of antibodies for targeted cancer therapy has gained much attention in the past few decades because of their safety, high specificity and effectiveness across different models (Fauvel and Yasri, 2014; Neves and Kwok, 2015). A9(B8) antibody is the first 'human and mouse cross-reactive' specific anti-ADAM17 inhibitory antibody (Kwok et al., 2014). Due to the unique binding features of A9(B8) antibody along with the favorable pharmacokinetic (PK) properties that we showed in this study, this antibody serves perfectly as a prototype drug to target ADAM17 in preclinical studies with both in vitro human cell-based assays and an in vivo mouse model of PDAC. In this study, A9(B8) IgG efficiently prevented the release of a number of cytokines and ErbB ligands, such as TNF-α and AREG both in vitro and in vivo.

Previous reports have also suggested that TNF-α expression was shown to be elevated during PDAC initiation process, and AREG was upregulated in pancreatic cancer to enhance pancreatic tumour growth through an autoregulated feedback loop (Busser et al., 2011; Funatomi et al., 1997; Zhao et al., 2016). Taken together, it suggests that A9(B8) IgG can potentially be developed as an effective therapeutic agent for pancreatic cancer.

Using an aggressive PDAC mouse model, Pdx1Cre; KrasG12D/+;Trp53flox/+ (KPflC), the applicant began to assess the therapeutic effects of the ADAM17 inhibitory antibody A9(B8) in vivo. Similar to the development of human PDAC, our KPflC mice showed full spectrum of pre-invasive PanIN lesions and PDAC. Consistent with previous mouse genetic studies in which homogeneous knockout of Adam17 greatly prevents malignant tumor formation (Ardito et al., 2012), it was found that application of A9(B8) IgG dramatically suppressed the transition of metaplastic acini into advanced epithelial neoplasia in KPflC mice. A9(B8) IgG did not completely prevent precursor formation in all treated animals because we observed more low-grade pancreatic lesions in A9(B8) IgG-treated mice compared to control mice. These observations demonstrate that inhibition of ADAM17 via A9(B8) IgG affects the progression of pre-invasive lesions to advanced PDAC.

Moreover, it has been suggested that the activation of ADAM17 promotes an epithelial-to-mesenchymal transition (EMT) in various types of cancer (Tang et al., 2016; Xu et al., 2016). Consistent with this notion, we found that inhibition of ADAM17 by A9(B8) IgG was able to suppress migration of human pancreatic carcinoma cells PANC-1. Our wound-healing study revealed that the addition of A9(B8) IgG significantly reduced the motility of PANC-1 cells. We also found that A9(B8) IgG treatment did not influence cell proliferation, illustrating that A9(B8) IgG-mediated suppression of cell migration was independent of cell growth. Since EMT may play important roles in pancreatic cancer invasion and metastases (Rhim et al., 2012). Further studies are needed to examine whether A9(B8) IgG has therapeutic effects on pancreatic cancer metastases in vivo.

At the completion of these experiments we now have some understanding of therapeutic efficacies of the anti-ADAM17 antibody A9(B8) IgG on pancreatic tumorigenesis.

The data provided herein show definitive evidence that inhibition of ADAM17 via A9(B8) IgG efficiently reduces the shedding of ErbB ligands and suppresses the progression of pre-invasive pancreatic lesions to advanced carcinoma.

REFERENCES

1. Ardito, C. M., Briggs, C. D., Crawford, H. C., 2008. Targeting of extracellular proteases required for the progression of pancreatic cancer. Expert opinion on therapeutic targets 12, 605-619.
2. Ardito, C. M., Gruner, B. M., Takeuchi, K. K., Lubeseder-Martellato, C., Teichmann, N., Mazur, P. K., Delgiorno, K. E., Carpenter, E. S., Halbrook, C. J., Hall, J. C., Pal, D., Briel, T., Herner, A., Trajkovic-Arsic, M., Sipos, B., Liou, G. Y., Storz, P., Murray, N. R., Threadgill, D. W., Sibilia, M., Washington, M. K., Wilson, C. L., Schmid, R. M., Raines, E. W., Crawford, H. C., Siveke, J. T., 2012. EGF receptor is required for KRAS-induced pancreatic tumorigenesis. Cancer Cell 22, 304-317.
3. Bardeesy, N., Aguirre, A. J., Chu, G. C., Cheng, K.-h., Lopez, L. V., Hezel, A. F., Feng, B., Brennan, C., Weissleder, R., Mahmood, U., Hanahan, D., Redston, M. S., Chin, L., DePinho, R. A., 2015. Both p16Ink4a and the p19Arf-p53 pathway constrain progression of pancreatic adenocarcinoma in the mouse. Proceedings of the National Academy of Sciences of the United States of America 103, 5947-5952.
4. Bartsch, J. W., Wildeboer, D., Koller, G., Naus, S., Rittger, A., Moss, M. L., Minai, Y., Jockusch, H., 2010. Tumor necrosis factor-alpha (TNF-alpha) regulates shedding of TNF-alpha receptor 1 by the metalloprotease-disintegrin ADAM8: evidence for a protease-regulated feedback loop in neuroprotection. The Journal of neuroscience: the official journal of the Society for Neuroscience 30, 12210-12218.
5. Basturk, O., Hong, S. M., Wood, L. D., Adsay, N. V., Albores-Saavedra, J., Biankin, A. V., Brosens, L. A., Fukushima, N., Goggins, M., Hruban, R. H., Kato, Y., Klimstra D. S., Kloppel, G., Krasinskas, A., Longnecker, D. S., Matthaei, H., Offerhaus, G. J., Shimizu, M., Takaori, K., Terris, B., Yachida, S., Esposito, I., Furukawa, T., 2015. A Revised Classification System and Recommendations From the Baltimore Consensus Meeting for Neoplastic Precursor Lesions in the Pancreas. The American journal of surgical pathology 39, 1730-1741.
6. Blanchot-Jossic, F., Jarry, A., Masson, D., Bach-Ngohou, K., Paineau, J., Denis, M. G., Laboisse, C. L., Mosnier, J. F., 2005. Up-regulated expression of ADAM17 in human colon carcinoma: co-expression with EGFR in neoplastic and endothelial cells. The Journal of pathology 207, 156-163.
7. Borrell-Pages, M., Rojo, F., Albanell, J., Baselga, J., Arribas, J., 2003. TACE is required for the activation of the EGFR by TGF-alpha in tumors. The EMBO journal 22, 1114-1124.
8. Busser, B., Sancey, L., Brambilla, E., Coill, J. L., Hurbin, A., 2011. The multiple roles of amphiregulin in human cancer. Biochimica et biophysica acta 1816, 119-131.
9. Cornish, T. C., Hruban, R. H., 2011. Pancreatic Intraepithelial Neoplasia. Surg Pathol Clin 4, 523-535.
10. Coussens, L. M., Fingleton, B., Matrisian, L. M., 2002. Matrix metalloproteinase inhibitors and cancer: trials and tribulations. Science 295, 2387-2392.
11. DasGupta, S., Murumkar, P. R., Giridhar, R., Yadav, M R., 2009. Current perspective of TACE inhibitors: a review. Bioorganic & medicinal chemistry 17, 444-459.
12. Fauvel, B., Yasri, A., 2014. Antibodies directed against receptor tyrosine kinases: current and future strategies to fight cancer. MAbs 6, 838-851.
13. Fridman, J. S., Caulder, E., Hansbury, M., Liu, X., Yang, G., Wang, Q., Lo, Y., Zhou, B. B., Pan, M., Thomas, S. M., Grandis, J. R., Zhuo, J., Yao, W., Newton, R. C Friedman, S. M., Scherle, P. A., Vaddi, K., 2007. Selective inhibition of ADAM metalloproteases as a novel approach for modulating ErbB pathways in cancer. Clinical cancer research: an official journal of the American Association for Cancer Research 13, 1892-1902.
14. Funatomi, H., Itakura, J., Ishiwata, T., Pastan, I., Thompson, S. A., Johnson, G. R., Korc, M., 1997. Amphiregulin antisense oligonucleotide inhibits the growth of T3M4 human pancreatic cancer cells and sensitizes the cells to EGF receptor-targeted therapy. International journal of cancer 72, 512-517.
15. Georgiadis, D., Yiotakis, A., 2008. Specific targeting of metzincin family members with small-molecule inhibitors: progress toward a multifarious challenge. Bioorganic & medicinal chemistry 16, 8781-8794.

16. Hidalgo, M., 2010. Pancreatic cancer. N Engl J Med 362, 1605-1617.

17. Hruban, R. H., Goggins, M., Parsons, J., Kern, S. E., 2000. Progression model for pancreatic cancer. Clin Cancer Res 6, 2969-2972.

18. Janes, R. H., Jr., Niederhuber, J. E., Chmiel, J. S., Winchester, D. P., Ocwieja, K. C., Karnell, J. H., Clive, R. E., Menck, H. R., 1996. National patterns of care for pancreatic cancer. Results of a survey by the Commission on Cancer. Ann Surg 223, 261-272.

19. Koorstra, J. B., Feldmann, G., Habbe, N., Maitra, A., 2008. Morphogenesis of pancreatic cancer: role of pancreatic intraepithelial neoplasia (PanINs). Langenbecks Arch Surg 393, 561-570.

20. Kopp, J. L., von Figura, G., Mayes, E., Liu, F. F., Dubois, C. L., Morris, J. P. t., Pan, F. C., Akiyama, H., Wright, C. V., Jensen, K., Hebrok, M., Sander, M., 2012. Identification of Sox9-dependent acinar-to-ductal reprogramming as the principal mechanism for initiation of ancreatic ductal adenocarcinoma.

21. Kwok, H. F., Botkjaer, K. A., Tape, C. J., Huang, Y., McCafferty, J., Murphy, G., 2014. Development of a 'mouse and human cross-reactive' affinity-matured exosite inhibitory human antibody specific to TACE (ADAM17) for cancer immunotherapy. Protein engineering, design & selection: PEDS 27, 179-190.

22. Kyula, J. N., Van Schaeybroeck, S., Doherty, J., Fenning, C. S., Longley, D. B., Johnston, P. G., 2010. Chemotherapy-induced activation of ADAM-17: a novel mechanism of drug resistance in colorectal cancer. Clinical cancer research: an official journal of the American Association for Cancer Research 16, 3378-3389.

23. Lee, M. H., Knauper, V., Becherer, J. D., Murphy, G., 2001. Full-length and N-TIMP-3 display equal inhibitory activities toward TNF-alpha convertase. Biochem Biophys Res Commun 280, 945-950.

24. Liu, X., Fridman, J. S., Wang, Q., Caulder, E., Yang, G., Covington, M., Liu, C., Marando, C., Zhuo, J., Li, Y., Yao, W., Vaddi, K., Newton, R. C., Scherle, P. A., Friedman, S. M., 2006. Selective inhibition of ADAM metalloproteases blocks HER-2 extracellular domain (ECD) cleavage and potentiates the anti-tumor effects of trastuzumab. Cancer Biol Ther 5, 648-656.

25. McGowan, P. M., Mullooly, M., Caiazza, F., Sukor, S., Madden, S. F., Maguire, A. A., Pierce, A., McDermott, E. W., Crown, J., O'Donovan, N., Duffy, M. J., 2013. ADAM-17: a novel therapeutic target for triple negative breast cancer. Annals of oncology: official journal of the European Society for Medical Oncology/ESMO 24, 362-369.

26. Moore, M. J., Goldstein, D., Hamm, J., Figer, A., Hecht, J. R., Gallinger, S., Au, H. J., Murawa, P., Walde, D., Wolff, R. A., Campos, D., Lim, R., Ding, K., Clark, G., Voskoglou-Nomikos, T., Ptasynski, M., Parulekar, W., National Cancer Institute of Canada Clinical Trials, G., 2007. Erlotinib plus gemcitabine compared with gemcitabine alone in patients with advanced pancreatic cancer: a phase III trial of the National Cancer Institute of Canada Clinical Trials Group. J Clin Oncol 25, 1960-1966.

27. Morton, J. P., Klimstra, D. S., Mongeau, M. E., Lewis, B. C., 2008. Trp53 deletion stimulates the formation of metastatic pancreatic tumors. Am J Pathol 172, 1081-1087.

28. Morton, J. P., Timpson, P., Karim, S. A., Ridgway, R. A., Athineos, D., Doyle, B., Jamieson, N. B., Oien, K. A., Lowy, A. M., Brunton, V. G., Frame, M. C., Evans, T. R., Sansom, O. J., 2010. Mutant p53 drives metastasis and overcomes growth arrest/senescence in pancreatic cancer. Proceedings of the National Academy of Sciences of the United States of America 107, 246-251.

29. Moss, M. L., Sklair-Tavron, L., Nudelman, R., 2008. Drug insight: tumor necrosis factor-converting enzyme as a pharmaceutical target for rheumatoid arthritis. Nature clinical practice. Rheumatology 4, 300-309.

30. Navas, C., Hernandez-Porras, I., Schuhmacher, A. J., Sibilia, M., Guerra, C., Barbacid, M., 2012. EGF receptor signaling is essential for k-ras oncogene-driven pancreatic ductal adenocarcinoma. Cancer Cell 22, 318-330.

31. Neves, H., Kwok, H. F., 2015. Recent advances in the field of anti-cancer immunotherapy. BBA Clin 3, 280-288.

32. Normanno, N., De Luca, A., Bianco, C., Strizzi, L., Mancino, M., Maiello, M. R., Carotenuto, A., De Feo, G., Caponigro, F., Salomon, D. S., 2006. Epidermal growth factor receptor (EGFR) signaling in cancer. Gene 366, 2-16.

33. Rhim, A. D., Mirek, E. T., Aiello, N. M., Maitra, A., Bailey, J. M., McAllister, F., Reichert, M., Beatty, G. L., Rustgi, A. K., Vonderheide, R. H., Leach, S. D., Stanger, B. Z., 2012. EMT and dissemination precede pancreatic tumor formation. Cell 148, 349-361.

34. Richards, F. M., Tape, C. J., Jodrell, D. I., Murphy, G., 2012. Anti-tumour effects of a specific anti-ADAM17 antibody in an ovarian cancer model in vivo. PloS one 7, e40597.

35. Sahin, U., Weskamp, G., Kelly, K., Zhou, H. M., Higashiyama, S., Peschon, J., Hartmann, D., Saftig, P., Blobel, C. P., 2004. Distinct roles for ADAM10 and ADAM17 in ectodomain shedding of six EGFR ligands. J Cell Biol 164, 769-779.

36. Sawey, E. T., Johnson, J. A., Crawford, H. C., 2007. Matrix metalloproteinase 7 controls pancreatic acinar cell transdifferentiation by activating the Notch signaling pathway. Proceedings of the National Academy of Sciences of the United States of America 104, 19327-19332.

37. Schlomann, U., Koller, G., Conrad, C., Ferdous, T., Golfi, P., Garcia, A. M., Hofling, S., Parsons, M., Costa, P., Soper, R., Bossard, M., Hagemann, T., Roshani, R., Sewald, N., Ketchem, R. R., Moss, M. L., Rasmussen, F. H., Miller, M. A., Lauffenburger, D. A., Tuveson, D. A., Nimsky, C., Bartsch, J. W., 2015. ADAM8 as a drug target in pancreatic cancer. Nature communications 6, 6175.

38. Tang, J., Xiao, L., Cui, R., Li, D., Zheng, X., Zhu, L., Sun, H., Pan, Y., Du, Y., Yu, X., 2016. CX3CL1 increases invasiveness and metastasis by promoting epithelial-to-mesenchymal transition through the TACE/TGF-alpha/EGFR pathway in hypoxic androgen-independent prostate cancer cells. Oncol Rep 35, 1153-1162.

39. Tape, C. J., Willems, S. H., Dombernowsky, S. L., Stanley, P. L., Fogarasi, M., Ouwehand, W., McCafferty, J., Murphy, G., 2011. Cross-domain inhibition of TACE ectodomain. Proceedings of the National Academy of Sciences of the United States of America 108, 5578-5583.

40. Valkovskaya, N., Kayed, H., Felix, K., Hartmann, D., Giese, N. A., Osinsky, S. P., Friess, H., Kleeff, J., 2007. ADAM8 expression is associated with increased invasiveness and reduced patient survival in pancreatic cancer. J Cell Mol Med 11, 1162-1174.

41. Van Schaeybroeck, S., Kyula, J. N., Fenton, A., Fenning, C. S., Sasazuki, T., Shirasawa, S., Longley, D. B., Johnston, P. G., 2011. Oncogenic Kras promotes chemotherapy-induced growth factor shedding via ADAM17. Cancer research 71, 1071-1080.
42. Wang, J. P., Wu, C. Y., Yeh, Y. C., Shyr, Y. M., Wu, Y. Y., Kuo, C. Y., Hung, Y. P., Chen, M. H., Lee, W. P., Luo, J. C., Chao, Y., Li, C. P., 2015. Erlotinib is effective in pancreatic cancer with epidermal growth factor receptor mutations: a randomized, open-label, prospective trial. Oncotarget 6, 18162-18173.
43. Warshaw, A. L., Fernandez-del Castillo, C., 1992. Pancreatic carcinoma. N Engl J Med 326, 455-465.
44. Woods, N., Trevino, J., Coppola, D., Chellappan, S., Yang, S., Padmanabhan, J., 2015. Fendiline inhibits proliferation and invasion of pancreatic cancer cells by interfering with ADAM10 activation and beta-catenin signaling. Oncotarget 6, 35931-35948.
45. Xu, M., Zhou, H., Zhang, C., He, J., Wei, H., Zhou, M., Lu, Y., Sun, Y., Ding, J. W., Zeng, J., Peng, W., Du, F., Gong, A., 2016. ADAM17 promotes epithelial-mesenchymal transition via TGF-beta/Smad pathway in gastric carcinoma cells. Int J Oncol 49, 2520-2528.
46. Zhang, Y., Hegen, M., Xu, J., Keith, J. C., Jr., Jin, G., Du, X., Cummons, T., Sheppard, B. J., Sun, L., Zhu, Y., Rao, V. R., Wang, Q., Xu, W., Cowling, R., Nickerson-Nutter, C. L., Gibbons, J., Skotnicki, J., Lin, L. L., Levin, J., 2004. Characterization of (2R, 3S)-2-([[4-(2-butynyloxy) phenyl]sulfonyl]amino)-N,3-dihydroxybutanamide, a potent and selective inhibitor of TNF-alpha converting enzyme. Int Immunopharmacol 4, 1845-1857.
47. Zhao, X., Fan, W., Xu, Z., Chen, H., He, Y., Yang, G., Yang, G., Hu, H., Tang, S., Wang, P., Zhang, Z., Xu, P., Yu, M., 2016. Inhibiting tumor necrosis factor-alpha diminishes desmoplasia and inflammation to overcome chemoresistance in pancreatic ductal adenocarcinoma. Oncotarget 7, 81110-81122.
48. Zheng, X., Jiang, F., Katakowski, M., Kalkanis, S. N., Hong, X., Zhang, X., Zhang, Z. G., Yang, H., Chopp, M., 2007. Inhibition of ADAM17 reduces hypoxia-induced brain tumor cell invasiveness. Cancer science 98, 674-684.
49. Zhou, B. B., Peyton, M., He, B., Liu, C., Girard, L., Caudler, E., Lo, Y., Baribaud, F., Mikami, I., Reguart, N., Yang, G., Li, Y., Yao, W., Vaddi, K., Gazdar, A. F., Friedman, S. M., Jablons, D. M., Newton, R. C., Fridman, J. S., Minna, J. D., Scherle, P. A., 2006. Targeting ADAM-mediated ligand cleavage to inhibit HER3 and EGFR pathways in non-small cell lung cancer. Cancer cell 10, 39-50.
50. Zhu, L., Shi, G., Schmidt, C. M., Hruban, R. H., Konieczny, S. F., 2007. Acinar cells contribute to the molecular heterogeneity of pancreatic intraepithelial neoplasia. Am J Pathol 171, 263-273.

What we claim is:

1. A method of treating pancreatic cancer which comprises suppressing ADAM 17 function by administering a therapeutic dose of a human-mouse cross-reactive ADAM 17 antibody having two heavy chains and two light chains wherein the heavy chains have the sequence set out in SEQ ID NO 1 and the light chains have the sequence set out in SEQ ID NO: 2 to a subject in need thereof.

2. The method as claimed in claim 1, wherein said cancer is pancreatic duct adrenal carcinoma.

3. The method as claimed in claim 1, wherein said cancer is pancreatic adenocarcinoma.

4. The method of claim 1, wherein said treatment is combined with treatment other chemo therapies for pancreatic cancer selected from treatments with as gemcitabine, FOLFORINOX and Erlotinib.

* * * * *